United States Patent
Jabbarzadeh et al.

(10) Patent No.: US 11,426,360 B2
(45) Date of Patent: Aug. 30, 2022

(54) PIMARANE DITERPENOIDS FOR USE IN WOUND HEALING AND ANGIOGENESIS

(71) Applicant: UNIVERSITY OF SOUTH CAROLINA, Columbia, SC (US)

(72) Inventors: Ehsan Jabbarzadeh, Columbia, SC (US); Sara Eslambolchimoghadam, Columbia, SC (US)

(73) Assignees: University of South Carolina, Columbia, SC (US); TIGHitco, Inc., North Charleston, SC (US)

(*) Notice: Subject to any disclaimer, the term of this patent is extended or adjusted under 35 U.S.C. 154(b) by 81 days.

(21) Appl. No.: 16/578,688

(22) Filed: Sep. 23, 2019

(65) Prior Publication Data

US 2020/0016090 A1    Jan. 16, 2020

Related U.S. Application Data

(62) Division of application No. 16/004,576, filed on Jun. 11, 2018, now Pat. No. 10,463,631.

(60) Provisional application No. 62/518,067, filed on Jun. 12, 2017, provisional application No. 62/634,244, filed on Feb. 23, 2018, provisional application No. 62/651,749, filed on Apr. 3, 2018.

(51) Int. Cl.
*A61K 31/047* (2006.01)
*A61K 31/05* (2006.01)
*A61P 17/02* (2006.01)

(52) U.S. Cl.
CPC ............ *A61K 31/047* (2013.01); *A61K 31/05* (2013.01); *A61P 17/02* (2018.01)

(58) Field of Classification Search
CPC ........ A61K 31/05; A61K 31/047; A61P 17/02
USPC ......................................................... 514/729
See application file for complete search history.

(56) References Cited

U.S. PATENT DOCUMENTS

| | | |
|---|---|---|
| 2018/0353439 A1 | 12/2018 | Jabbarzadeh et al. |
| 2018/0353457 A1 | 12/2018 | Jabbarzadeh et al. |
| 2018/0369165 A1 | 12/2018 | Jabbarzadeh et al. |

OTHER PUBLICATIONS

Gadir et al, Journal of Chemical and Pharmaceutical Research (2014), vol. 6 (7), pp. 151-156. (Year: 2014).*
Boateng et al, Journal of Pharmaceutical Sciences (2008), vol. 97(8), pp. 2892-2923. (Year: 2008).*
Seca et al., Natural Product Communications 2008, vol. 3(3), pp. 399-412 (Year: 2008).*
Basmadjian, et al. "Cancer Wars: Natural Products Strike Back" *Front. Chem.* 2(20) (2014) pp. 1-18.
Burmistrova, et al. "Antiproliferative Activity of Abietane Diterpenoids Against Human Tumor Cells" *J Nat. Prod.* 76(8) (2013) pp. 1413-1423.

(Continued)

*Primary Examiner* — Craig D Ricci
*Assistant Examiner* — Janet L Coppins
(74) *Attorney, Agent, or Firm* — Dority & Manning, P.A.

(57) ABSTRACT

Methods and compositions are described for use in encouraging angiogenesis and skin healing as may be utilized in wound treatment as well as in encouragement of angiogenesis in disease. Compositions include an effective amount of a natural pimarane diterpenoid extract of *Hymenocrater elegans*, or a derivative, analogue, or homolog thereof. Compounds based upon this natural extract have been found to be highly effective in vascular formation and skin closure while exhibiting low toxicity.

14 Claims, 14 Drawing Sheets

(56) References Cited

OTHER PUBLICATIONS

Decicco-Skinner, et al. "Endothelial cell tube formation assay for the in vitro study of angiogenesis" *J Visual. Exper.* 91:e51312 (2014) pp. 1-8.

Driver, et al. "The costs of diabetic foot: the economic case for the limb salvage team" *J Vasc. Surg.* 52(3) (2010) pp. 17S-22S.

Hosseinzadeh, et al. "Review of the Pharmacological and Toxicological Effects of *Salvia leriifolia*" *Iran. J Basic Med. Sci.* 12(1) 2009, pp. 1-8.

Hussein, et al. "New adduct of abietane-type diterpene from *Salvia leriifolia* Benth." *Nat Prod Res*, 30(13), 2016, pp. 1511-1516.

Kuhn, et al. "Balancing the pressure ulcer cost and quality equation" *Nursing economic$*, (10(5) (1991) pp. 353-359.

Merck & Co. "The Merck Index—14$^{th}$ ed." Whitehouse Station, NJ (2006). https://www.rsc.org/merck-index.

Newman, et al. "Natural Products as Sources of New Drugs Over the Last 25 Years" *J Nat. Prod.* 70(3) (2007) pp. 461-477.

Sen, et al. "Human skin wounds: a major and snowballing threat to public health and the economy" *Wound Rep. Regen.* 17(6) (2009) pp. 763-771.

Siegel, et al. "Cancer Statistics 2016" *CA: Cancer J Phys.* 66(1) (2016) pp. 7-30.

Singer, et al. "Cutaneous wound healing" *New Eng. J Med.* 341(10) (1999) pp. 738-746.

Tecilazich, et al. "Emerging drugs for the treatment of diabetic ulcers" *Expert Opin. Emerg. Drugs* 18(2) (2013) pp. 207-217.

Wang, et al. "Enhanced keratinocyte proliferation and migration in co-culture with fibroblasts" *PloS One* 7(7):e40951 (2012) pp. 1-12.

Wang, et al. "Anti-Proliferative Effect of Jesridonin on Paclitaxel-Resistant EC109 Human Esophageal Carcinoma Cells" *Intl. J Molec. Med.* 39 (2017) pp. 645-653.

Zhang, et al. "Oridonin Effectively Reverses the Drug Resistance of Cisplatin Involving Induction of Cell Apoptosis and Inhibition of MMP Expression in Human Acute Myeloid Leukemia Cells" *Saudi J Biol. Sci.* 24(3) (2017) pp.678-686.

\* cited by examiner

PIMARANE DITERPENOIDS FOR USE IN WOUND HEALING AND ANGIOGENESIS

CROSS REFERENCE TO RELATED APPLICATION

This application is a divisional application of U.S. patent application Ser. No. 16/004,576, which claims filing benefit of U.S. Provisional Patent Application Ser. No. 62/518,067, entitled "Use of a Newly Discovered Pimarane Diterpenoid for Wound Healing," having a filing date of Jun. 12, 2017; United States Provisional Patent Application Ser. No. 62/634,244, entitled "Use of a Newly Discovered Pimarane Diterpenoid for Wound Healing," having a filing date of Feb. 23, 2018; and U.S. Provisional Patent Application Ser. No. 62/651,749, entitled "Pimarane Diterpenoids for Use in Wound Healing and Angiogenesis," having a filing date of Apr. 3, 2018, all of which being incorporated herein by reference for all purposes.

FEDERAL RESEARCH STATEMENT

This invention was made with government support under Grant No. 1631439, awarded by the National Science Foundation. The government has certain rights in the invention.

BACKGROUND

The successful treatment of wounds to regenerate healthy and functional skin remains a huge challenge due to the skin's multilayered structure, the presence of multiple different cell types organized within the extracellular matrix, and different biochemical pathways present in different wound types (e.g., acute wounds, chronic wounds, burns, etc.). An aging population and its requisite medical interventions, the continuing rise in diabetes and obesity, and an increase in the occurrence of traumatic wounds all translate to large increases in skin wounds needing treatment.

Particularly problematic are chronic non-healing wounds, which are estimated to affect approximately 2% of the general U.S. population. Patients with these hardest-to-heal wounds include those with diabetes, sickle cell ulcers, vasculitis, and scleroderma, as well as obese individuals. The cost of caring for chronic wounds in the U.S. alone is reported to exceed $50 billion annually.

While wound healing technology has grown rapidly, offering new products applicable for both acute (including both traumatic and surgical wounds) and chronic wound management, need for further improvement exists. For example, it is estimated that among the 2 million people diagnosed yearly with pressure ulcers, 900,000 remain non-healing after initial treatment, and reports indicate that of 800,000 diabetic foot ulcers treated in the U.S. yearly, 30% don't respond to common treatments.

Currently marketed drugs for use in severe wound treatment include Regranex® (Becarplermin), a genetically engineered recombinant platelet-derived growth factor, silver-based products such as silver sulfadiazine and Silvadene®, and wound dressings loaded with active ingredients such as silver, bismuth, chlorhexidine, bacitracin, hydrocortisone, or lidocaine. Growth factors such as transforming growth factor beta and fibroblast growth factors as well as Living Skin Equivalents (LSEs) are another class of advanced wound care products. Other products include different classes of keratolytics, antiseptics, sulfa-antibiotics, and collagen-specific enzymes. Many currently available wound healing medications are based on growth factors, cytokines, chemokines, collagen or hyaluronic acid. There are disadvantages associated with such agents due to side effects including inflammatory response and undesired stimulation of other cell types. There are also reported side effects for silver-containing products including bacterial resistance, cytotoxic effects, and hepatic or renal toxicity.

Such issues call for alternative wound healing agents that can provide more effective and rapid wound treatments with fewer side effects. Safer compounds that can promote the epithelialization and vascular formation in both acute and chronic wounds as well as other applications calling for similar activities would be of great benefit.

Natural products provide a historically successful source of medicinally active compounds and have the potential to provide targeted healing responses while limiting the undesirable side effects associated with many currently utilized treatments. Wound therapies based on natural compounds such as plant extracts and natural active components offer viable alternatives to synthetic pharmaceuticals, enhancing access to healthcare, and overcoming limitations associated with synthetic products and therapies, including high costs, long manufacturing times, and increased bacterial resistance.

SUMMARY

According to one embodiment, disclosed is a method for treatment of a wound. A method can include application of a composition to the wound, the composition including a pimarane diterpenoid having the following structure (I):

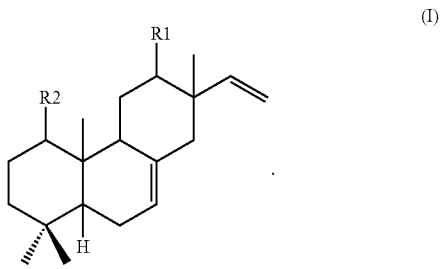

or a tautomer thereof in which $R_1$ and $R_2$ are independently selected from —H, $C_{1-10}$ alkyl, alkoxy, alkenyl, alkenoxy, —OH, —OAc, —CHO, -Ph, —$OC_6H_5$, —$OC_6H_4OH$, —$COC_6H_5$, —$OCONH_2$, —$OCONHCH_3$, —$OCOC_6H_4NH_2$, —$NH_2$, or =O.

In one embodiment, $R_1$ and $R_2$ can both be hydroxyl groups, and the compound can have the following structure (II):

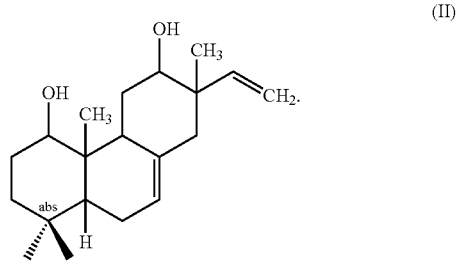

Beneficially, disclosed methods are applicable to different types of wounds including chronic wounds, acute wounds, and burns.

Also disclosed are methods for encouraging angiogenesis in an area. A method can include application of a composition to the area, the composition including a pimarane diterpenoid of structure (I). Encouragement of angiogenesis may be useful in in treatment of diseases that do not necessarily encompass wound treatment.

Also disclosed are compositions that include a pimarane diterpenoid of structure (I) in conjunction with a biocompatible carrier. Disclosed compositions can include a pimarane diterpenoid of structure (I) in conjunction with other active ingredients, which can vary depending, for example, on the type of wound for which the composition is intended or for which the particular disease being treated by use of the composition.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
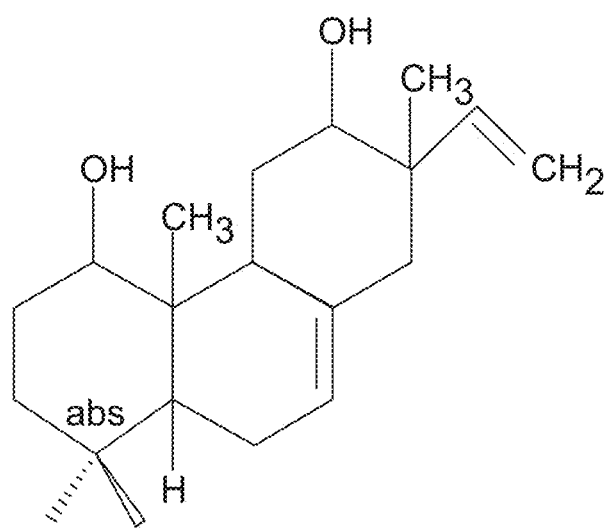
FIG. 1 presents the structure of a natural pimarane diterpenoid extract as described herein.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed herein are methods and compositions for use in encouraging angiogenesis and/or skin healing as may be utilized in wound treatment, as well as in treatment of disease in which increased angiogenesis is desirable. Disclosed compounds are based on a natural extract that can show efficacy in the prevention or treatment of disorders or pathologies of the skin, vascular disorders and/or problems linked to hyperseborrhea, or can be used as an anti-aging, healing, moisturizing, or pro-pigmenting agent, among other uses.

Compositions disclosed herein can include an effective amount of a pimarane diterpenoid having the following structure:

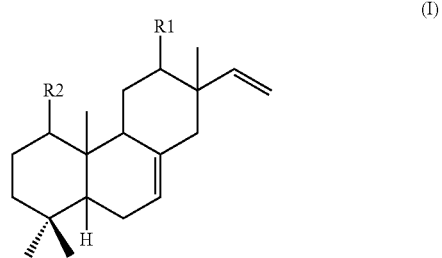

(I)

or a tautomer thereof in which $R_1$ and $R_2$ are independently selected from —H, $C_{1-10}$ alkyl, alkoxy, alkenyl, alkenoxy, —OH, —OAc, —CHO, -Ph, —OC$_6$H$_5$, —OC$_6$H$_4$OH, —COC$_6$H$_5$, —OCONH$_2$, —OCONHCH$_3$, —OCOC$_6$H$_4$NH$_2$, —NH$_2$, or =O.

Disclosed compounds have been derived from a natural extract of *Hymenocrater elegans*. *Hymenocrater* is a genus of plants from the mint family. It is native to central and southwestern Asia from Turkey to Turkmenistan and Pakistan. The genus *Hymenocrater* contains essential oils, with flavonoids, phenolic acids, and terpenoids being major constituents of the genus. Pharmacological studies have confirmed that certain species of the genus *Hymenocrater* show antimicrobial, antiparasitic, antioxidant, anticancer, and antidiabetic activities. *Hymenocrater elegans*, also generally known as *Hymenocrater elegans* Bunge, is one of several species of this genus. *H. elegans* is widely distributed throughout Iran. Oil extracted from *H. elegans* has been shown to exhibit concentration-dependent antibacterial activity on *B subtilis*, *S. aureus*, *E. coli* and *Salmonella typhi*, but constituents of this species have not previously been shown to exhibit wound healing or angiogenic activity. The pimarane diterpenoid of illustrated in FIG. 1 (structure II) was isolated from *H. elegans* and purified before being exposed, in vitro, to cells associated with wound healing and angiogenesis, as described further herein.

As described in more detail herein, compounds based upon this natural extract have been found to be highly effective in vascular formation and skin closure while exhibiting low toxicity.

In vitro experiments using the purified extract, details of which are described further herein, have revealed a cell-specific and dose-dependent response for multiple types of skin and wound-related cells. In addition, the purified extract and analogs as encompassed herein can demonstrate low toxicity and show efficacy as an extracellular pro-motility factor of several cell types that carry out important physiologic roles in early and late stages of wound healing. The combination of low toxicity with the ability to promote vascular formation and skin wound closure can be of great benefit, and disclosed compounds can be utilized in treatment of skin injuries in a variety of applications. For example, disclosed compounds can be used in combination with other known treatments in different stages of a wound healing process to enhance efficacy in various clinical applications.

Natural bioactive agents usually modulate multiple phases of the healing process, acting through a number of targets by inducing anti-inflammatory, antioxidant, and antibacterial effects. Similar to other natural bioactive agents, and unlike most modalities that only target one aspect of wound healing, disclosed compounds can simultaneously enhance multiple beneficial biochemical mechanisms. For instance, disclosed compounds can simultaneously promote the wound healing activities of keratinocytes and fibroblasts while also enhancing vascular tube formation.

Wound-healing encompasses multiple physiological processes including inflammation, cell proliferation, neovascularization, tissue granulation, re-epithelialization, and tissue reorganization. Re-epithelization involves migration and proliferation of epithelial tissue, primarily keratinocytes, and occurs in early wound repair. Angiogenesis is marked by endothelial cell migration and capillary formation responsible for delivering nutrients to the wound and helping maintain the granulation tissue bed. The final step of the proliferative phase is granulation tissue formation. Fibroblasts differentiate and produce ground substance as well as deposit collagen. Beneficially, disclosed compounds can encourage desirable activity at multiple stages of the wound healing process by various mechanisms including antimicrobial, anti-inflammatory, antioxidant, collagen synthesis stimulation, cell proliferative cell-stimulating and angiogenesis properties.

Compounds based upon the disclosed natural extract can be effective in treatment of any type of wound in either external tissue (e.g., skin) or internal tissue (e.g., digestive system, internal surgical sites). Non-limiting examples of wounds and skin injuries that can be treated by disclosed compositions include first, second, or third degree burn wounds resulting from exposure to heat, electricity, radiation (for example, sunburn or laser surgery), caustic chemicals, etc.; ulcers; hemorrhoids; wounds in diabetes mellitus; wounds, bedsores, and lesions caused by unrelieved pressure to any part of the body (especially portions over bony or cartilaginous areas); wounds due to external force damaging the tissue; skin wounds due to aging or the environment including splits, dry skin, roughness of the skin and the like; and ischemic syndromes such as coronary or peripheral arterial disease and angiogenesis-dependent disease. However, it should be understood that compositions based on the disclosed natural extract have the potential to be effective against many other forms of wounds and skin disease outside of this small subset, and the use of this these compounds can be applied to the treatment of wounds, the prevention of scars, and the encouragement of angiogenesis in an array of diseases.

Compounds based on the disclosed extract can be provided in combination with other materials, including active agents and biocompatible carrier materials. Particular materials for use in conjunction with compounds based on the disclosed extract can vary, depending upon the particular application of the composition. For instance, the extract (or a derivative thereof, as described above) can be used alone or in combination with other products as a supplement or cosmetic. The compounds can be effective when formulated as skin conditioning, UV protective, or antiaging products in the form of a cream, a gel, an ointment, or a skin pad. More potent activities may be achievable for other applications of wound healing, for instance through semi-synthesis to augment its potential or in combination with other compounds.

A composition including a compound derived from the disclosed extract can be administered in any number of formats known to current pharmaceutical practice including, without limitation, solid wound dressings, gels, creams, ointments, liquid wound washers, etc. A composition may be stored for future use or may be formulated in effective amounts in conjunction with pharmaceutically acceptable carriers to prepare a wide variety of pharmaceutical compositions that can be stored or immediately used according to known practice. For instance, the compounds and/or compositions including the compounds can be protected from light and refrigerated to prolong the lifetime their use.

Disclosed compounds can be combined with any pharmaceutically acceptable carrier, adjuvant, or vehicle in formation of a composition. Examples of pharmaceutically acceptable carriers include, without limitation, pharmaceutical appliances, topical vehicles (non-oral and oral), ingestible vehicles and so forth. In addition, a pharmaceutical composition can be made using manufacturing techniques and processes readily known to those skilled in the art.

Compositions can be combined with pharmaceutical appliances for delivery to a wound or other area. Examples of pharmaceutical appliances include, without limitation, sutures, staples, gauze, bandages, burn dressings, artificial skins, liposome or micelle formulations, microcapsules, aqueous articles for soaking gauze dressings, and so forth.

In addition, ingestible compositions desirably can employ ingestible or partly ingestible vehicles such as confectionery bulking agents which include hard and soft vehicles, such as, for example, tablets, suspensions, chewable candies or gums, lozenges and so forth.

Topical compositions may employ one or more carriers or vehicles such as, for example, creams, gels, foams, ointments, sprays, salves, bio-adhesives, films, fabrics and so forth, which are intended to be applied to the skin or a body cavity. Topical compositions may also be adapted for use as an oral vehicle such as, for example, mouthwashes, rinses, oral sprays, suspensions, and dental gels, which are intended to be taken by mouth but are not intended to be ingested. Topical ointments and other semi-solid compositions commonly employ one or more bases as a vehicle for drug delivery. Exemplary bases include, but are not limited to, hydrocarbon bases (e.g., white petrolatum, white ointment, vegetable oils, animals fats, etc.), absorption bases (e.g., hydrophilic petrolatum, anhydrous lanolin, lanolin, cold cream, etc.), water-removable bases (e.g., hydrophilic ointment USP, ethoxylated fatty alcohol ethers, ethoxylated lanolin derivatives, sorbitan fatty acid esters, etc.), and water-soluble bases (e.g., polyethylene glycol ointment, etc.).

A variety of traditional ingredients may optionally be included in the compositions in effective amounts. By way of non-limiting example, the compositions can contain one or more of the following materials: fillers, diluents, cleaning agents, buffers, preservatives, pH and toxicity modifiers, mechanical protectants, chemical protectants, adsorbents, antioxidants, viscosity modifiers, extenders, excipients, astringents, emollients, demulcents, humectants, emulsifiers, transdermal delivery enhancing agents, controlled-release agents, dyes or colorants, stabilizers, lubricants and so forth. These and other additives known to those having ordinary skill in the arts can be used in a composition as dictated by the nature of the delivery vehicle.

The amounts of additional components within the compositions are readily determined by those skilled in the art without the need for undue experimentation and will vary with the nature of the vehicle (e.g., a gel versus a spray), the wound to be treated, frequency of treatment and so forth. Thus, the amount of wound healing composition may be varied in order to obtain the result desired in the final product and such variations are within the capabilities of those skilled in the art without the need for undue experimentation. In a particular embodiment, a composition can comprise the disclosed extract (or a derivative or combination of derivatives thereof) in an amount of about 50 wt. % or less and in a further embodiment in an amount of about 20 wt. % or less by weight of the composition. In a further embodiment, a composition can contain the disclosed extract (or a derivative or combination of derivatives thereof) in an amount between about 0.00001% to about 5%, by weight of the composition. In an alternate embodiment, a composition can include the disclosed extract (or a derivative or combination of derivatives thereof) in an amount between about 0.001% to about 1%, by weight of the composition.

The clinical application and dosage of compounds based upon this extract can be tailored to the skin condition or disease, patient size, medical history, method of delivery, etc.

Disclosed compounds can synergize with other known compounds for a single application or can be initially applied to an area so as to initiate migration and tube formation prior to the application of a second active agent, e.g., another known wound healing compound.

As described below, use of disclosed compounds can simultaneously provide an accelerated rate of wound healing in major physiological components of the wound healing process, which demonstrates the effectiveness of the compounds as wound healing agent. Results show reduced time of wound closure of keratinocyte using a composition including the natural extract of FIG. 1 compared to the control (growth media) after multiple different time intervals. In addition, disclosed compounds can encourage vascular tubular network formation on a par with VEGF and cells treated with disclosed compositions can demonstrate a significant increase in tube formation as compared to negative controls.

The present disclosure may be better understood with reference to the Examples set forth below.

EXAMPLE

Instruments

Figure 2:
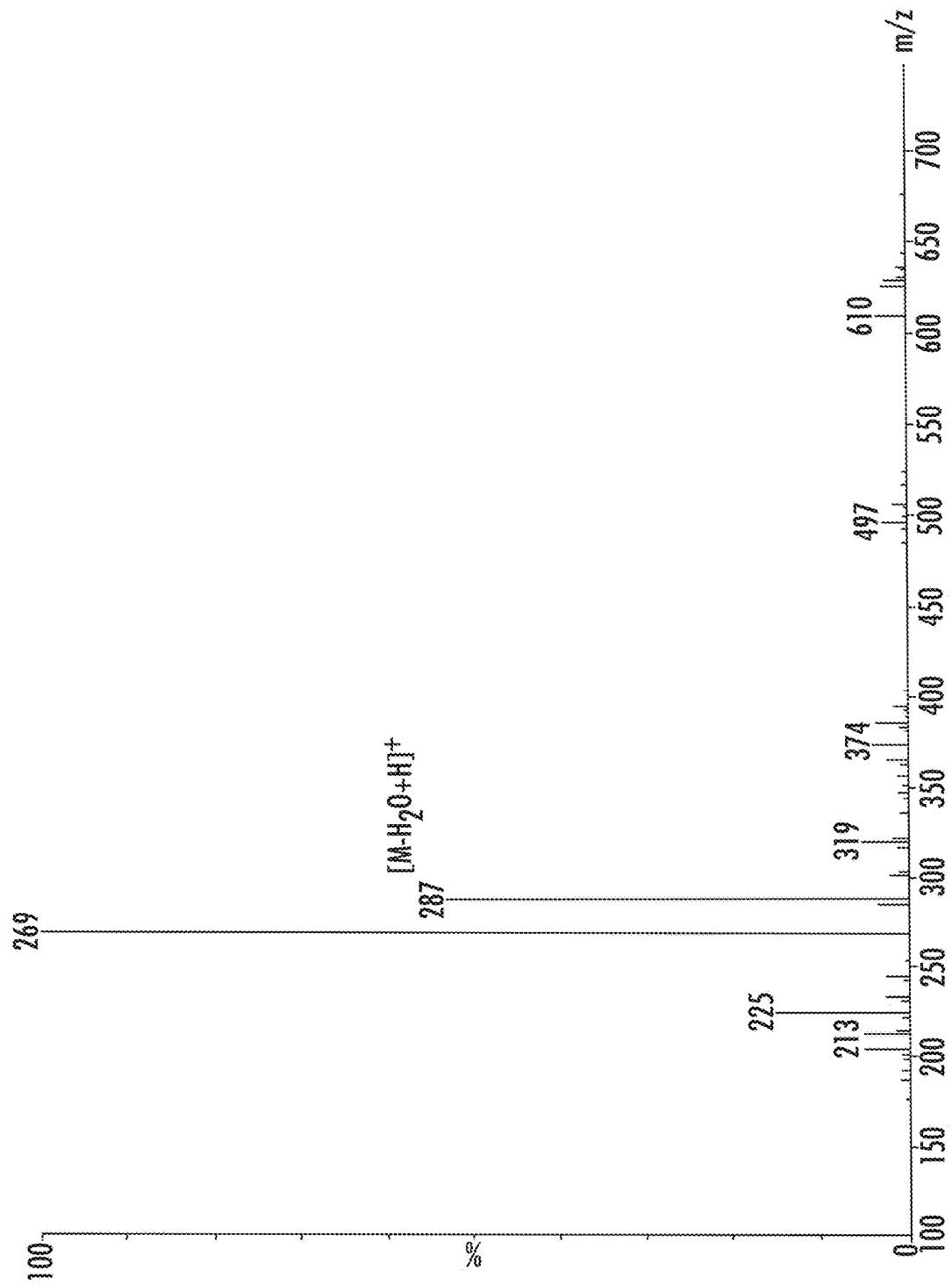
FIG. 2 presents the time of flight-mass spectrometry (TOF-MS) results (positive ion mode) for a pimarane diterpenoid having a structure as illustrated in FIG. 1.
Figure 3:
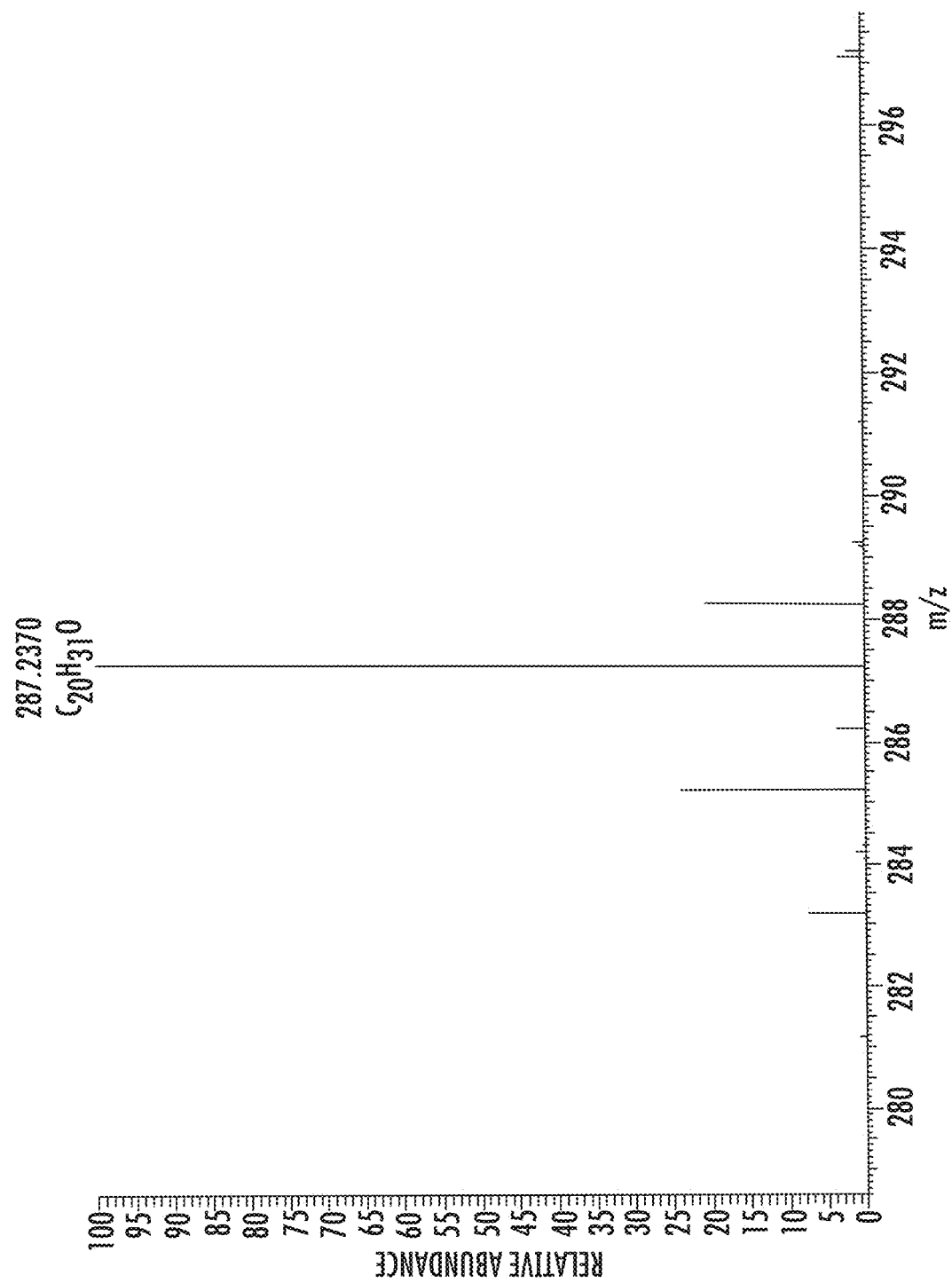
FIG. 3 presents the high resolution-mass spectrometry (HR-MS) results (positive ion mode) for a pimarane diterpenoid having a structure as illustrated in FIG. 1.
Figure 4:
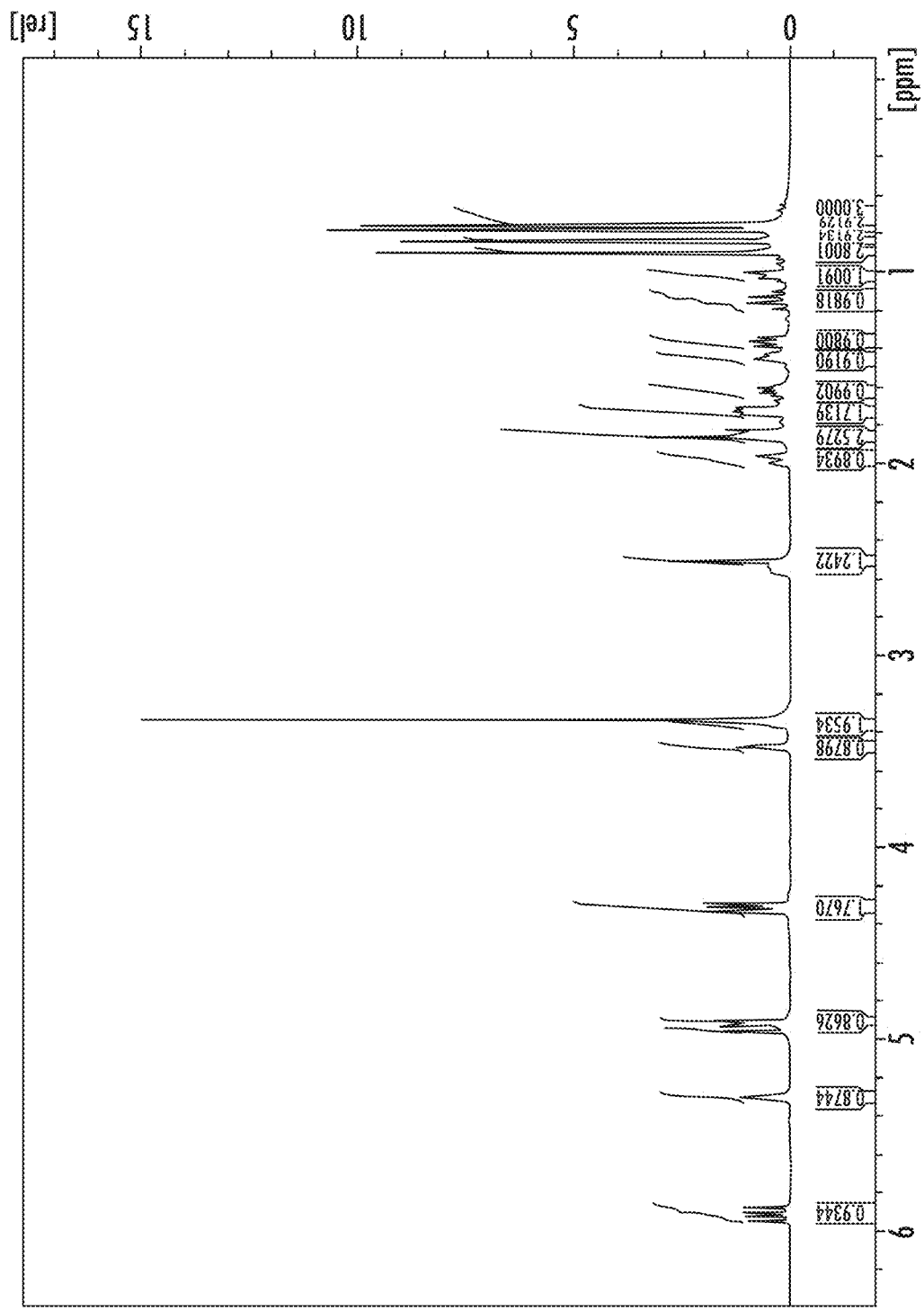
FIG. 4 presents the $^1$H-NMR spectrum for a pimarane diterpenoid having a structure as illustrated in FIG. 1.
Figure 5:
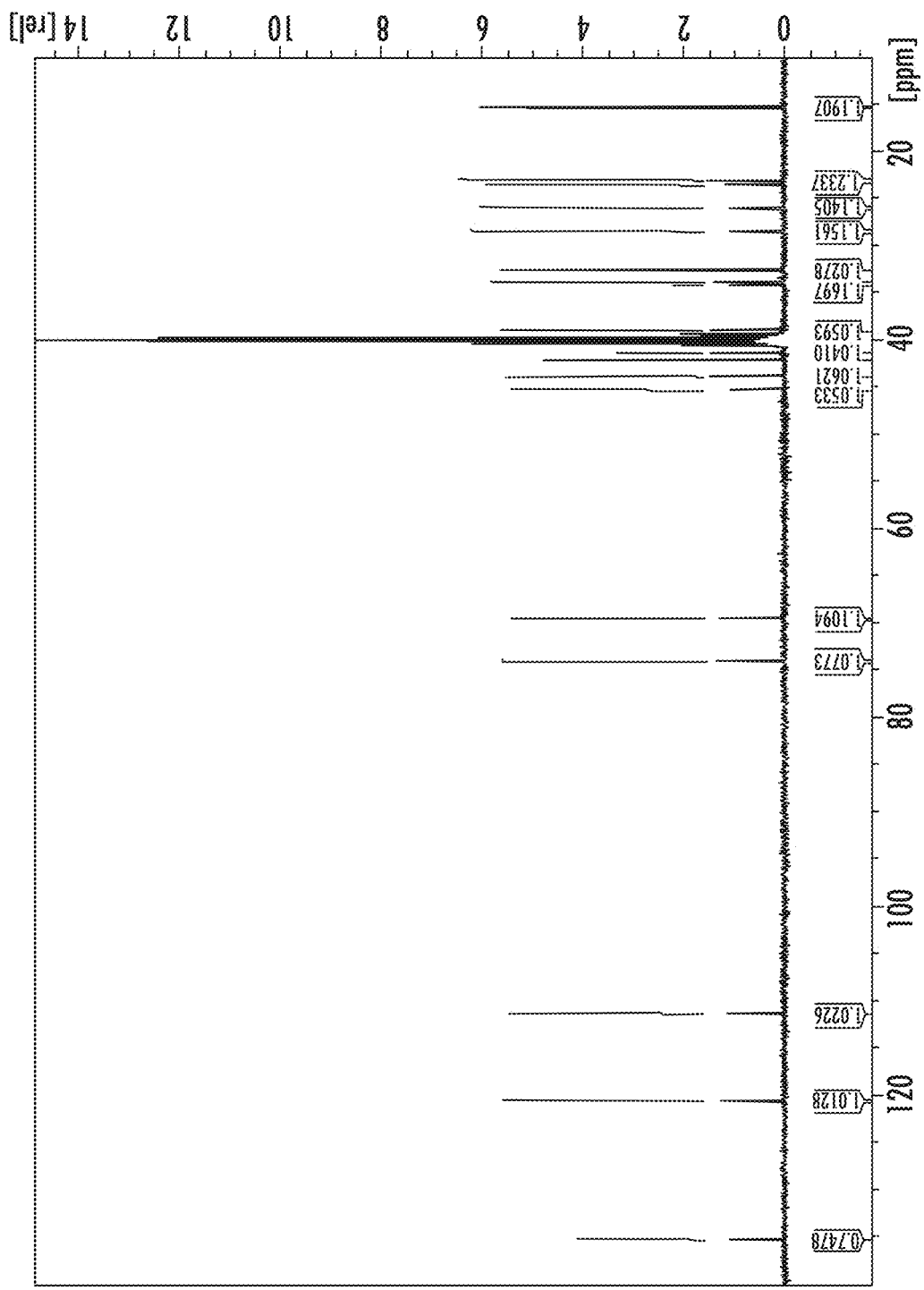
FIG. 5 presents the $^{13}$C-NMR spectrum for a pimarane diterpenoid having a structure as illustrated in FIG. 1.
Figure 6:
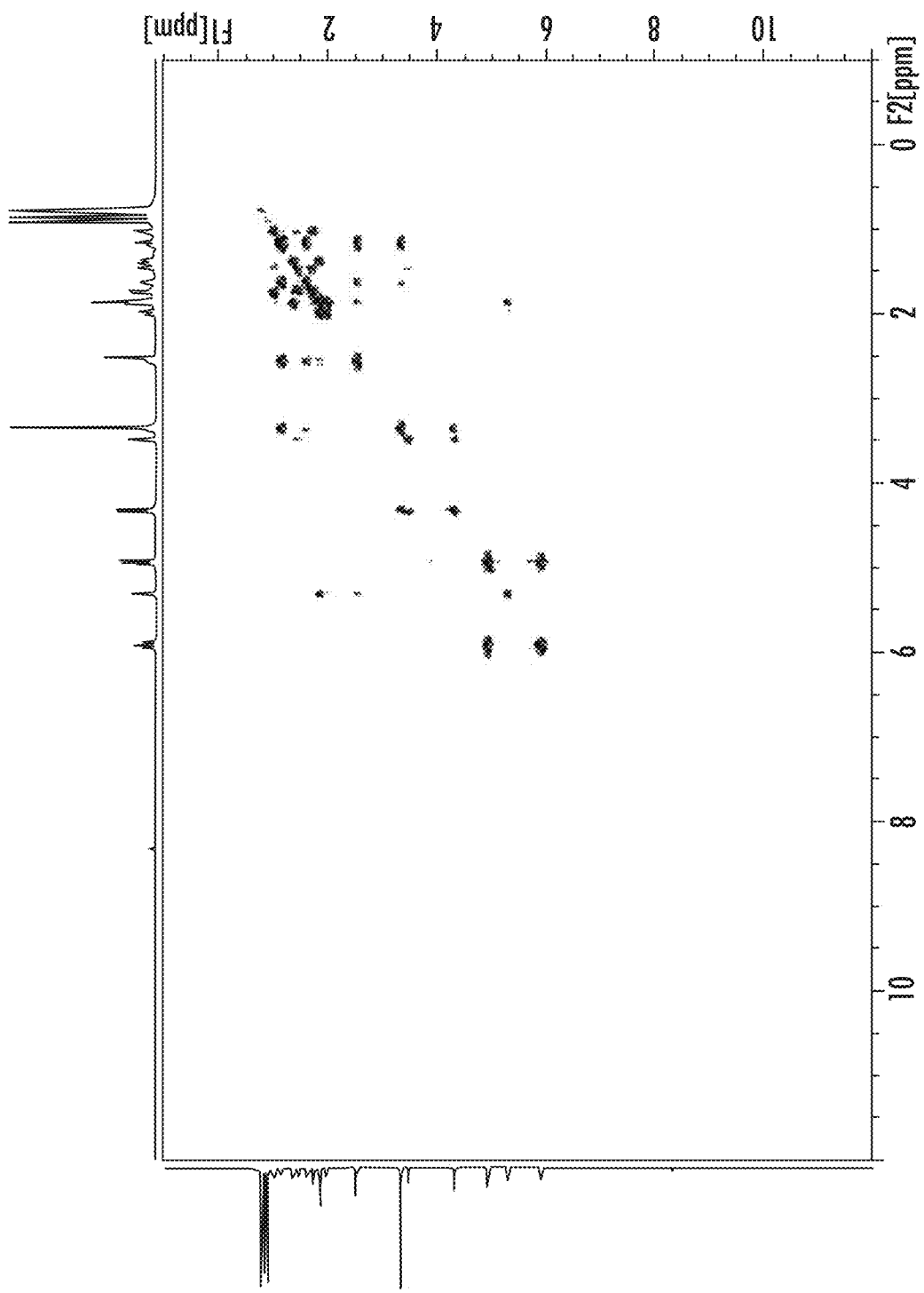
FIG. 6 presents the H—H correlated spectroscopy (COSY) spectrum for a pimarane diterpenoid having a structure as illustrated in FIG. 1.
Figure 7:
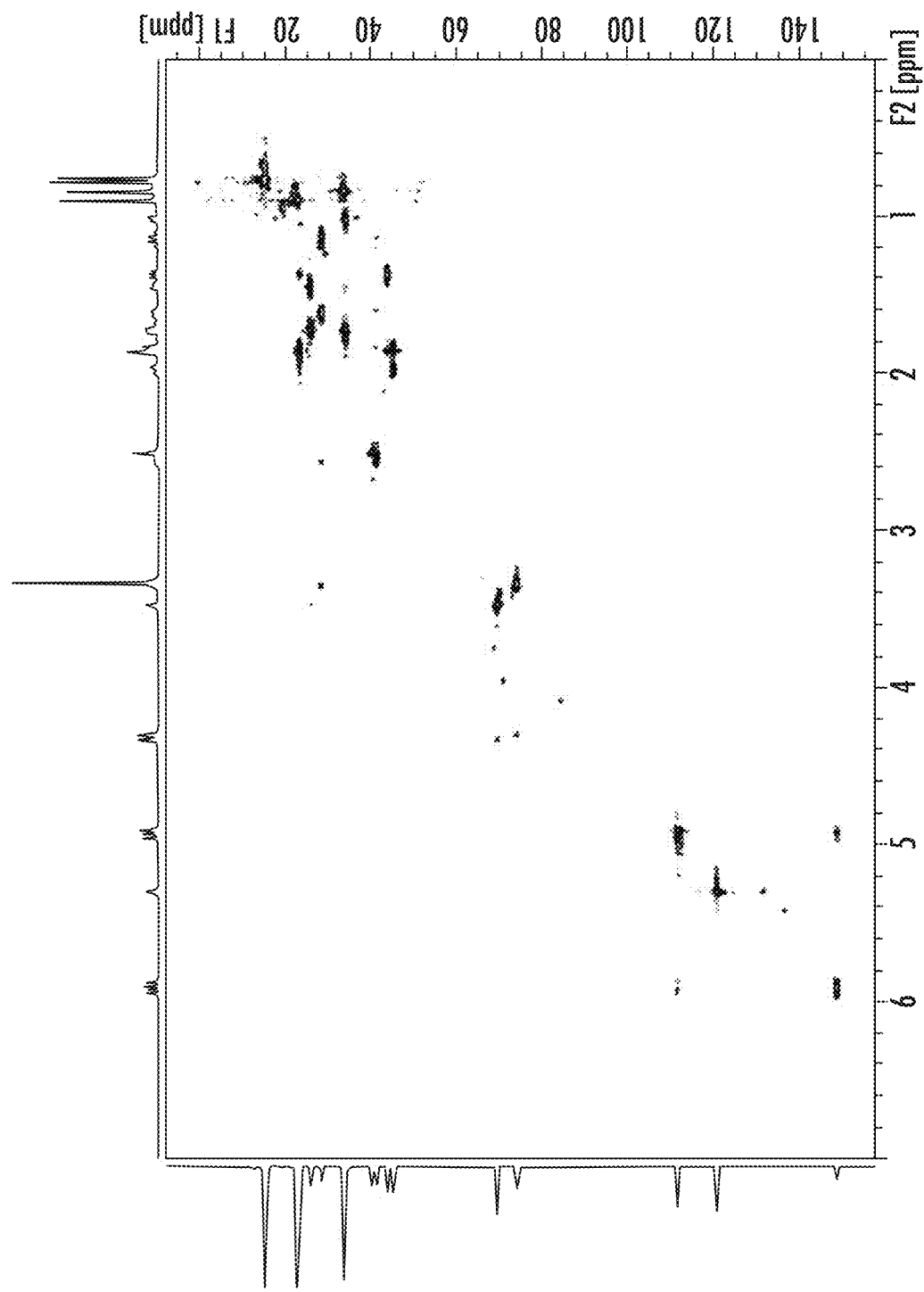
FIG. 7 presents the heteronuclear single quantum coherence (HSQC) spectrum for a pimarane diterpenoid having a structure as illustrated in FIG. 1.
Figure 8:
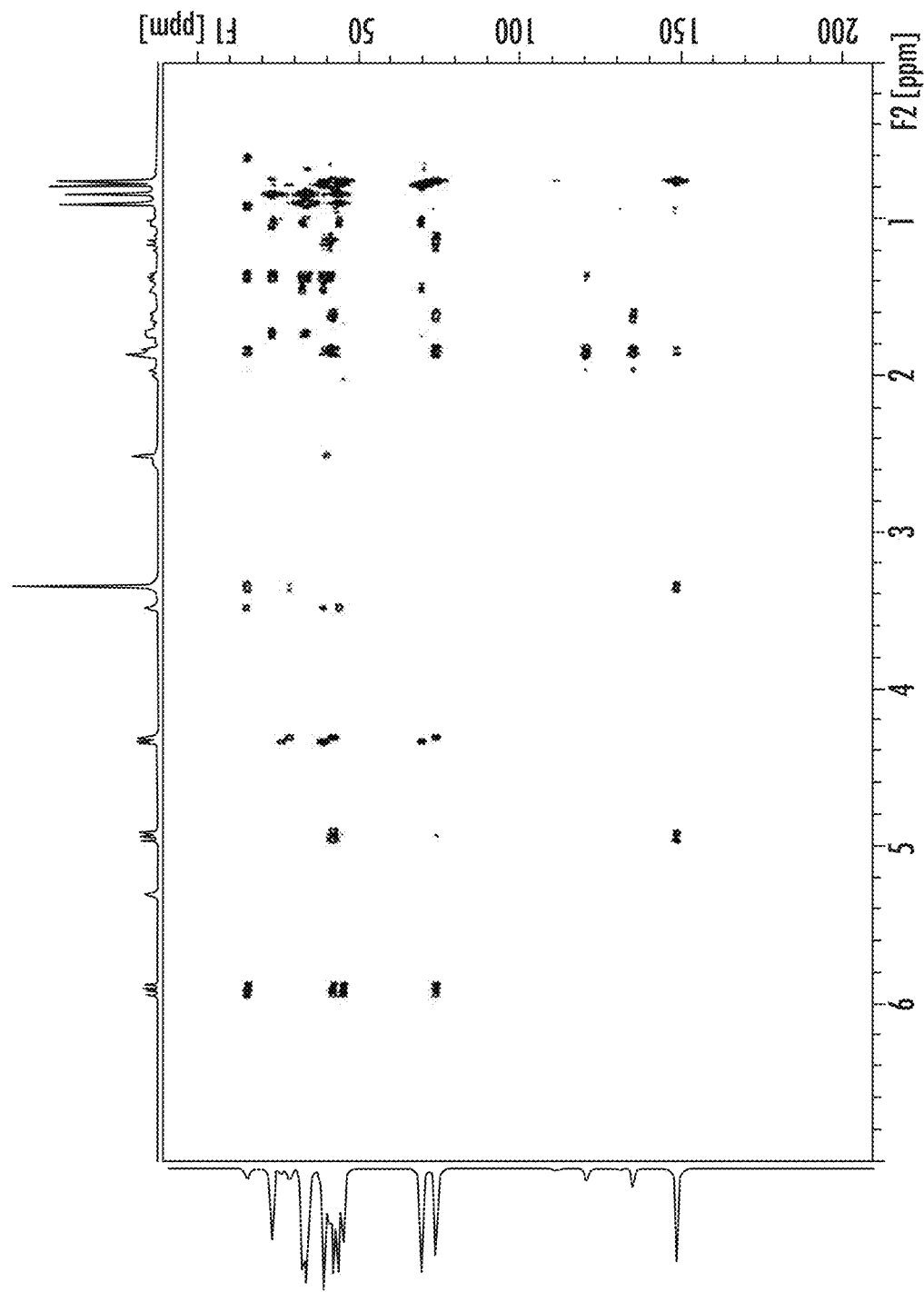
FIG. 8 presents the heteronuclear Multiple Bond Correlation (HMBC) spectrum for a pimarane diterpenoid having a structure as illustrated in FIG. 1.

The structure of the pimarane diterpenoid of FIG. 1 was established by means of 1D- and 2D-Nuclear Magnetic Resonance (NMR) (COSY (FIG. 6), HSQC (FIG. 7), and HMBC (FIG. 8)) and the molecular formula was determined by High Resolution Mass Spectrometry (HR-MS) (FIG. 3) and low resolution Time of Flight Mass Spectrometry (TOF-MS) (FIG. 2). NMR spectra (FIG. 4, FIG. 5) were obtained in DMSO-d6.

Cell Culture and Reagents

Human umbilical vein endothelial cells (HUVECs), adult normal human epidermal keratinocytes (NHEKs), normal human dermal fibroblasts (NHDFs) and related media for cell culture including endothelial basal and growth medium-2 (EBM-2, EGM-2), keratinocyte basal and growth medium-2 (KBM-2, KGM™-2), fibroblast basal and growth medium (FBM, FGM™) were purchased from Lonza. Cells were incubated at 37° C. and 5% $CO_2$ throughout the experiments. Phosphate-Buffered Saline (PBS), [3-(4,5-dimethylthiazol-2-yl)-5-(3-carboxymethoxyphenyl)-2-(4-sulfophenyl)-2H-tetrazolium (MTS) (Promega) colorimetric assay and growth factor reduced matrigel BD (Corning) were from Sigma-Aldrich. Culture-Insert 2 Well 24 IbiTreat was used for the scratch assay.

Cytotoxicity Assay (MTS)

In order to determine cell viability, HUVECs, NHDFs, NHEKs were cultured in their respective growth media to reach 80% confluency. Cells were seeded at the density of $3 \times 10^3$ cell per 96 well plate in a total volume of 100 µl in each well. After seeding, the cells were incubated for 24 hours at 37° C. and 5% $CO_2$ to allow for cell attachment. Media was changed and replaced with media supplemented with the desired concentration of the compound of interest (0.1, 0.5, 1 and 10 µg/mL), being first dissolved at 10,000 µg/mL in DMSO and subsequently diluted in culture media. The vehicle control was culture medium supplemented with DMSO 0.1% (Macron Fine Chemicals), representing the highest final concentration of DMSO used to dissolve the natural compound. Following 24 hours of incubation, media containing 20% MTS solution was replaced with growth media and incubated for 2 hours. Colored formazan absorbance which was produced by bio-reduction of MTS tetrazolium compound in live cells was read at 490 nm using a Spectramax 190 spectrophotometer and cell proliferation was assessed. A standard calibration curve at different concentration of cells was prepared to correlate cell number to absorbance.

In Vitro Scratch Assay

Cell migration of NHEKs was assessed through making a cell-free gap with a Culture-insert 2 well 24, consisting of two wells that were separated by a wall. A total of 70 µl of cell suspension comprising of $35 \times 10^3$ cell was applied in each well. Cells were given 24 hours to attach and reach confluency. Culture inserts were then removed, and cell debris was washed with PBS. The samples were supplemented with different concentration of the compound of interest in growth media and incubated at 37° C. and 5% $CO_2$ for 20 hours. Images were taken every 4 hours using a phase contrast Nikon Eclipse Ti-E inverted microscope. Quantification of percent wound healing was performed by measuring the gap distance using the following formula:

$$\text{Wound closure \%} = \frac{(W_0 - W_n)}{W_0} * 100\%$$

in which $W_n$ is the width of gap after every 4 hours and $W_0$ is the initial width zero right after forming a scratch.

Capillary Tube Formation

Matrigel was kept in a −20° C. freezer and thawed on ice overnight in a 4° C. refrigerator. A total of 50 µl of thawed matrigel was added to each well of pre-chilled 96-well plate and then incubated for 30 min at 37° C. to form a gel. Next, 100 µl of a HUVEC cell suspension (passage 2-6) in conditioned media (20000 cell/well), including the compound of this invention, was added to gel and incubated at 37° C. for 8 hours. The number of junctions in tubes was examined using a phase contrast inverted microscope (Invitrogen EVOS FL Auto Cell Imaging) and compared to the conditions with no compound (negative control) and VEGF growth factor (positive control).

Results

The pimarane diterpenoid natural extract of FIG. 1 was found to have a molecular formula of $C_{20}H_{32}O_2$ (evidenced by TOF-MS and HR-MS ([M-H$_2$O+H]$^+$ ion at m/z 287.2370 (FIG. 2, FIG. 3)). The NMR spectra (FIG. 4-FIG. 8) confirmed structure indicating loss of water in mass analysis. Resonance at δ 0.75 (s), 0.78 (s), 0.84 (s), and 0.90 (s) were indicative of four methyl groups at positions C-4, C-10, and C-13 of the molecule. Resonances in the region of δ 1.0 to 2.0 were attributed to the hydrogens of diterpenoid backbone. Chemical shifts at δ 5.32 (s), 5.91 (dd), 4.94 (dd), and 4.94 (dd) were indicators of olefinic hydrogens. Complementary assignment was obtained through the analysis of 2D spectra. The NMR spectra confirmed pimarane diterpenoid structure.

Figure 9:
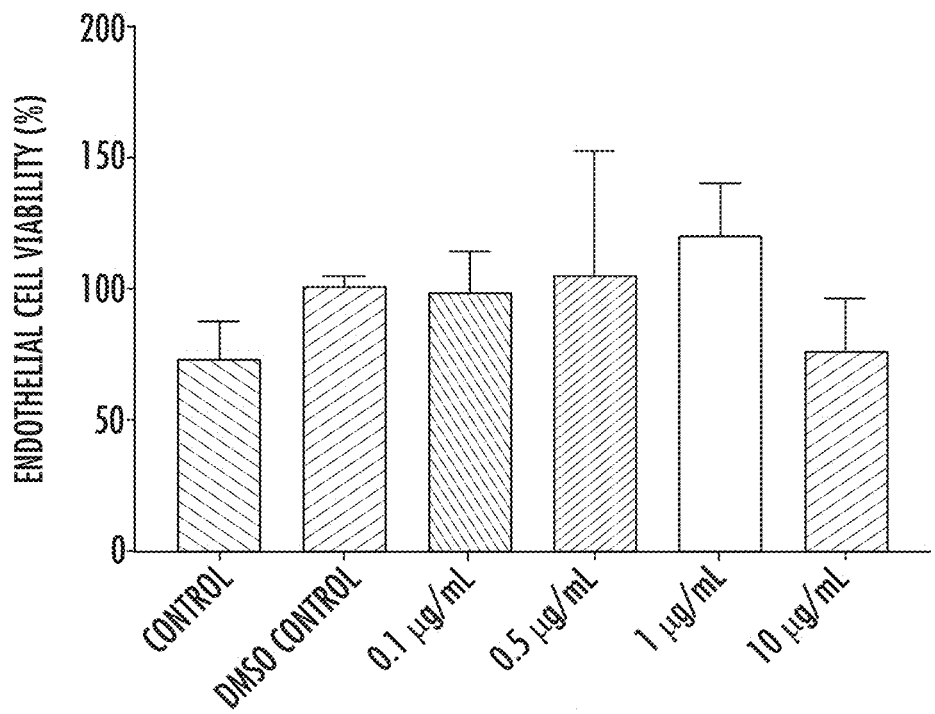
FIG. 9 illustrates the dose dependent cell proliferation of human umbilical vascular endothelial cells (HUVECs) in response to various concentrations of the compound of FIG. 1 after 24 hours of exposure calculated using an MTS assay.
Figure 10:
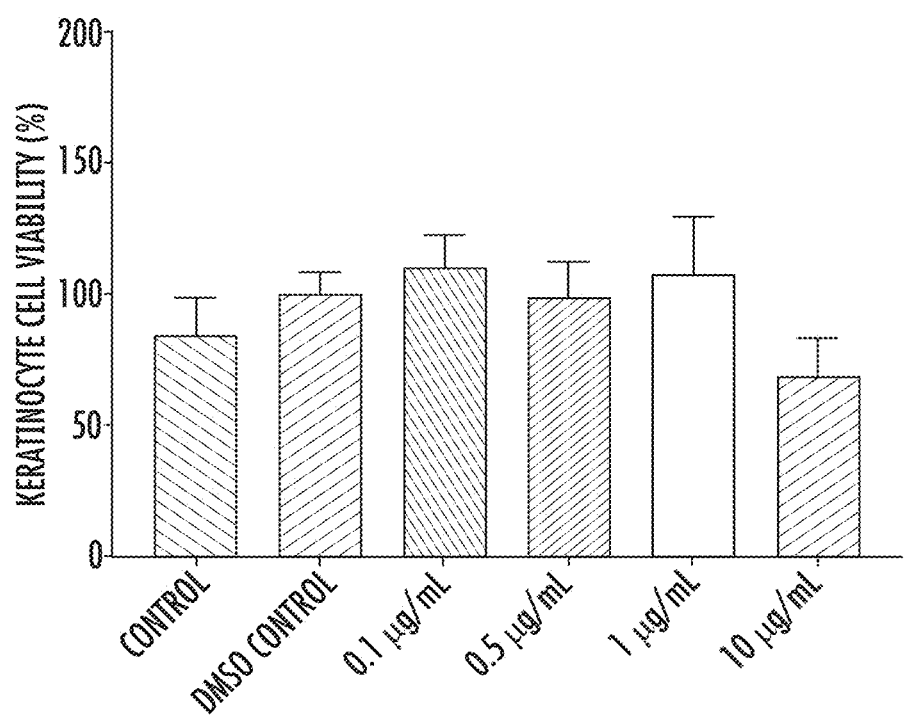
FIG. 10 illustrates the dose dependent cell proliferation of Normal Human Epidermal Keratinocytes (NHEKs) in response to various concentrations of the compound of FIG. 1 after 24 hours of exposure calculated using an MTS assay.
Figure 11:
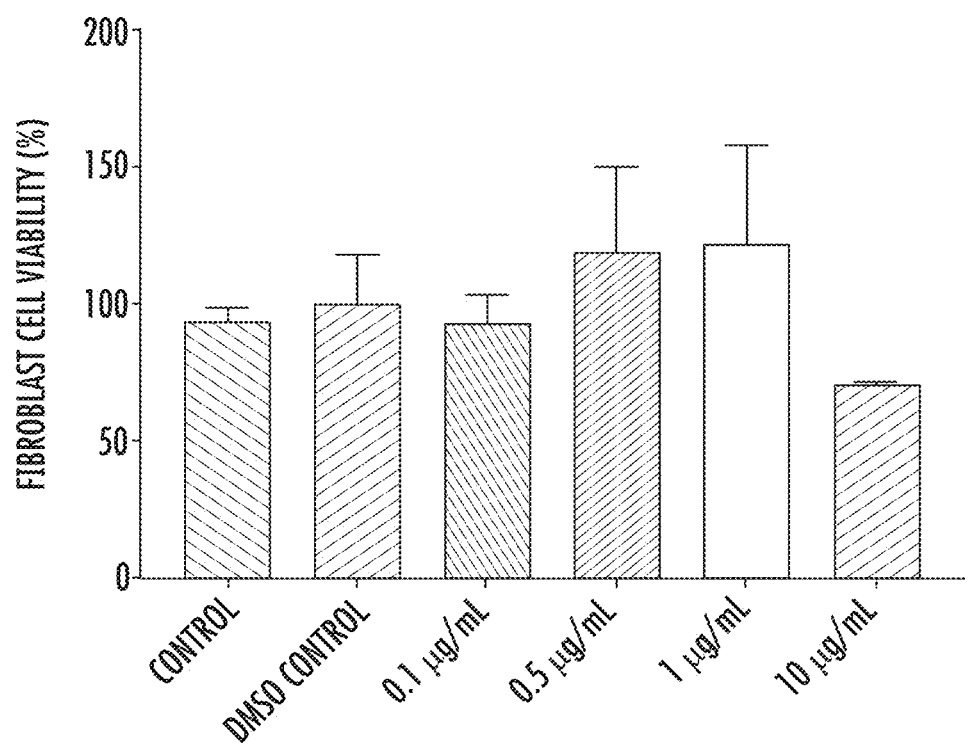
FIG. 11 illustrates the dose dependent cell proliferation of Normal Human Dermal Fibroblasts (NHDFs) in response to various concentrations of the compound of FIG. 1 after 24 hours of exposure calculated using an MTS assay.

Cell proliferation and viability results were analyzed at 24 hours post seeding to find optimum concentrations of the compound for angiogenesis and wound closure based on cytotoxicity analysis. As shown in FIG. 9, FIG. 10, and FIG. 11, no cell toxicity was observed after 24 hours of exposure to the three dermal and epidermal cell lines at concentrations between 0.1 to 1 µg/mL as compared to the control (untreated cells in growth media) and vehicle control (untreated cells in growth media containing control DMSO).

Figure 12:
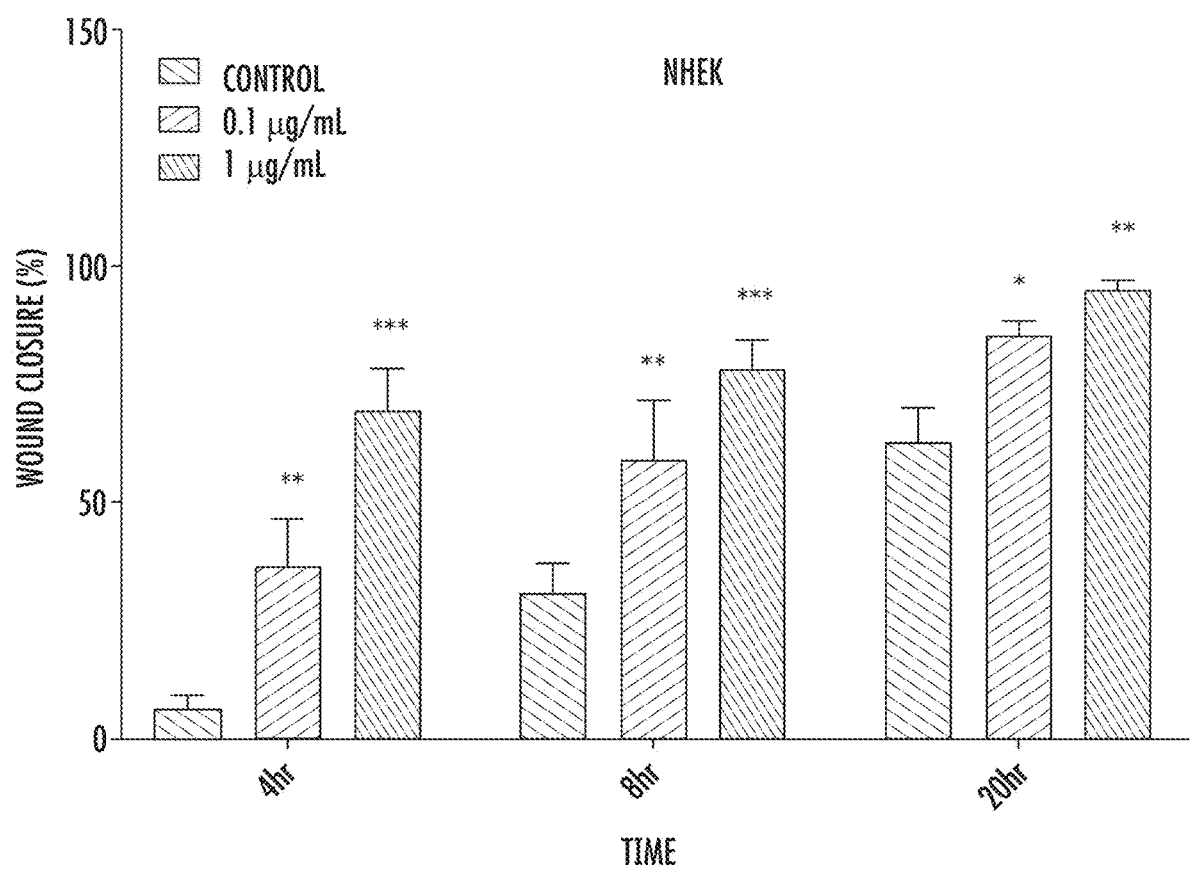
FIG. 12 illustrates the results of a migration assay carried out with the pimarane diterpenoid of FIG. 1 showing wound closure percentages of NHEKs after different time intervals of exposure to different concentrations of the compound.
Figure 13:
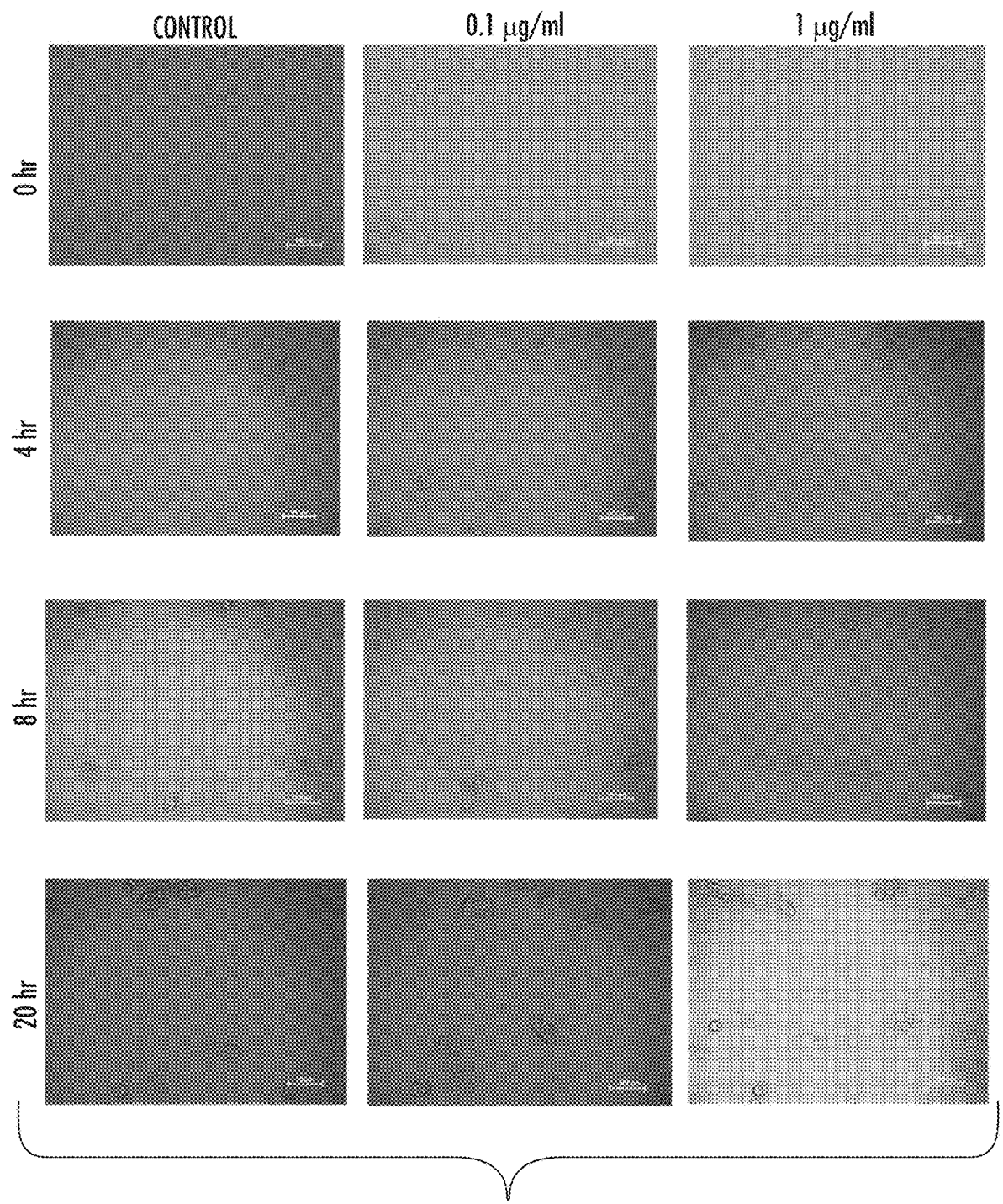
FIG. 13 illustrates results of an in vitro scratch assay carried out with NHEKs.

NHEKs were scratched and cell migration with and without treatment was monitored for 20 hours. The pimarane diterpenoid at concentrations of 0.1 and 1 µg/mL was found to significantly enhance the wound closure of NHEKs. Specifically, it was observed that at four hours post-treatment, the percentage of wound closure with samples containing 1 µg/mL of the compound was nearly 10-fold greater than that of non-treated control groups. This trend was valid until 20 hours after the treatment when the cells had nearly completed closing the wound (FIG. 12). A concentration of 1 µg/mL showed the highest migration during exposure time, as compared with the untreated cell and those treated with 0.1 µg/mL. Multiple t-tests were performed using Graph-Pad Prism 7.03 to determine the significance between each experimental group and control (*p≤0.05, p≤0.01, and *p≤0.001). The time progression of wound healing is demonstrated in a series of images taken from NHEKs migrating to fill the scratch (FIG. 13). Wound closure analysis was independent of mechanism.

Figure 14:
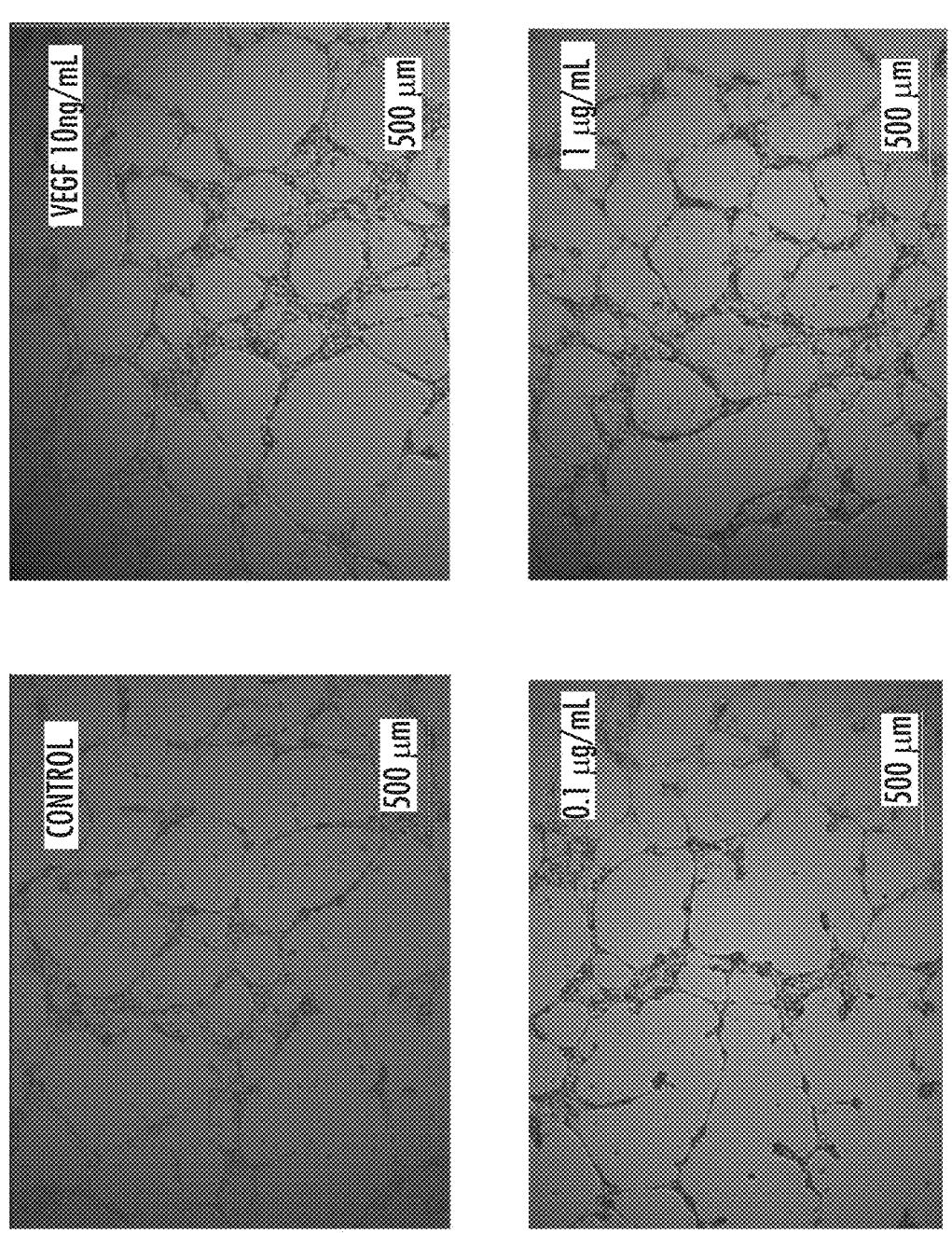
FIG. 14 illustrates in vitro capillary tube formation of HUVECs treated without a control, with a positive control (vascular endothelial growth factor, VEGF) or with different concentrations of a composition including the compound of FIG. 1.
Figure 15:
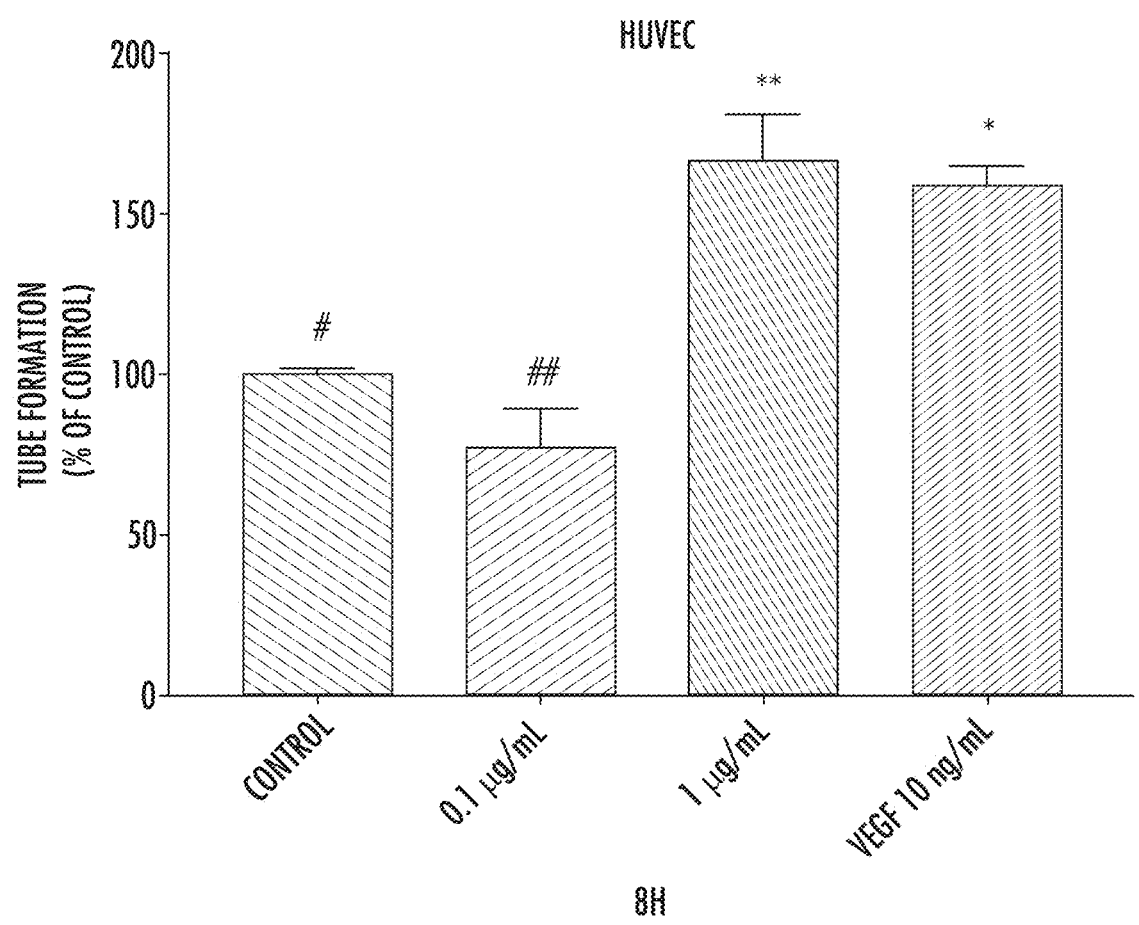
FIG. 15 compares the tube formation for the different compositions as a percentage of the control group.

As illustrated in FIG. 14 and FIG. 15, the treatment of HUVECs on matrigel with an effective dose of the compound of FIG. 1, 1 µg/mL, demonstrated the highest degree of tube formation, 60% more than the control (untreated cell). The quantitative analysis of the data showed that the effect was clearly visible at 8 hours (FIG. 15). The compound demonstrated similar efficacy to VEGF growth factor at 10 ng/m L. VEGF is traditionally used for the treatment of diabetic wound ulcers and as a potent angiogenesis inducer. Multiple t-tests were performed using Graph-Pad Prism 7.03 to determine the significance between each experimental group and control (*p≤0.05 and **p≤0.01). T-tests were performed to compare pure compound group to VEGF positive control (#p≤0.05 and ##p≤0.01). The results indicate promising pro-angiogenic activity of the pure compound. The data supports the potential of this compound as a wound healing agent.

While certain embodiments of the disclosed subject matter have been described using specific terms, such description is for illustrative purposes only, and it is to be understood that changes and variations may be made without departing from the spirit or scope of the subject matter.

What is claimed is:

1. A composition comprising a biocompatible carrier and a compound of structure (II):

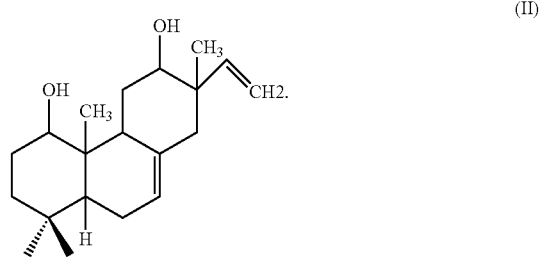

(II)

2. The composition of claim 1, wherein the composition is a component of a pharmaceutical appliance.

3. The composition of claim 2, the pharmaceutical appliance comprising a suture, a staple, gauze, a bandage, a solid wound dressing, or an artificial skin.

4. The composition of claim 1, the composition comprising a gel, a cream, a suspension, or an ointment.

5. The composition of claim 1, wherein the composition is contained within a capsule.

6. The composition of claim 1, the composition comprising the compound of structure (II) in an amount of about 50 wt. % or less by weight of the composition.

7. The composition of claim 1, the composition comprising the compound of structure (II) in an amount of between about 0.00001% to about 5% of the composition.

8. The composition of claim 1, the composition comprising the compound of structure (II) in an amount of from about 10 to about 100 micrograms per milliliter of the composition.

9. The composition of claim 1, wherein the composition is ingestible.

10. The composition of claim 1, wherein the composition is a topical composition.

11. The composition of claim 10, wherein the composition is held in conjunction with a carrier or vehicle.

12. The composition of claim 11, wherein the carrier comprises a foam, spray, salve, bio-adhesive, film, or fabric.

13. The composition of claim 1, wherein the composition comprises one or more of: a filler, a diluent, a cleaning agent, a buffer, a preservative, a pH modifier, a toxicity modifier, a mechanical protectant, a chemical protectant, an adsorbent, an antioxidant, a viscosity modifier, an extender, an excipient, an astringent, an emollient, a demulcent, a humectant, an emulsifier, a transdermal delivery enhancing agent, a controlled-release agent, a dye or colorant, a stabilizer, or a lubricant.

14. The composition of claim 1, wherein the composition is contained within a liposome or micelle.

* * * * *